US010416015B2

United States Patent
Xie et al.

(10) Patent No.: US 10,416,015 B2
(45) Date of Patent: Sep. 17, 2019

(54) REPRESENTATIVE SAMPLING OF MULTIPHASE FLUIDS

(71) Applicant: Schlumberger Technology Corporation, Sugar Land, TX (US)

(72) Inventors: Cheng-Gang Xie, Singapore (SG); Jianhua Zhu, Singapore (SG); Alexander Tuborg Vilstrup, Singapore (SG); Guillaume Jolivet, Singapore (SG); Shasha Wang, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 139 days.

(21) Appl. No.: 15/204,207

(22) Filed: Jul. 7, 2016

(65) Prior Publication Data
US 2018/0010944 A1    Jan. 11, 2018

(51) Int. Cl.
*G01F 1/74*    (2006.01)
*G01F 1/44*    (2006.01)
(Continued)

(52) U.S. Cl.
CPC .............. *G01F 1/74* (2013.01); *B01F 5/0652* (2013.01); *G01F 1/44* (2013.01); *G01N 1/38* (2013.01); *G01N 2001/205* (2013.01)

(58) Field of Classification Search
CPC ............ G01N 1/10; G01N 1/38; G01N 33/18; G01N 33/26; G01N 33/2847
(Continued)

(56) References Cited

U.S. PATENT DOCUMENTS 4,091,835 A * 5/1978 Frampton .............. G05D 7/012
                                                       137/499
4,144,754 A    3/1979 Pitts, Jr. et al.
(Continued)

FOREIGN PATENT DOCUMENTS

CN    203216545 U    9/2013
DE    9218091    7/1993
(Continued)

OTHER PUBLICATIONS

International Search Report and Written Opinion issued in the related PCT application PCT/US2016/030165 dated Aug. 4, 2016 (13 pages).
(Continued)

*Primary Examiner* — Benjamin R Schmitt
(74) *Attorney, Agent, or Firm* — Cameron R. Sneddon

(57) ABSTRACT

A technique facilitates evaluation of a fluid, such as a fluid produced from a well. The technique utilizes a modular and mobile system for testing flows of fluid which may comprise mixtures of constituents, and for sampling fluids thereof. The multiphase sampling method includes flowing a multiphase fluid comprising an oil phase and a water phase through a first conduit, the oil phase and water phase at least partially separating in the first conduit, mixing together the oil phase and water phase to form a mixed bulk liquid phase by flowing the multiphase fluid through a flow mixer toward a second conduit downstream the flow mixer, sampling a portion of the mixed bulk liquid phase at location at or within the second conduit, wherein the sampled portion of the mixed bulk liquid phase has a water-to-liquid ratio (WLR) representative of the pre-mixed oil phase and water phase.

11 Claims, 5 Drawing Sheets

(51) Int. Cl.
*B01F 5/06* (2006.01)
*G01N 1/38* (2006.01)
*G01N 1/20* (2006.01)

(58) Field of Classification Search
USPC .................................. 73/61.43, 61.44, 64.56
See application file for complete search history.

(56) References Cited

U.S. PATENT DOCUMENTS

| | | | |
|---|---|---|---|
| 4,760,742 | A | 8/1988 | Hatton |
| 5,390,547 | A | 2/1995 | Liu |
| 5,589,642 | A | 12/1996 | Agar et al. |
| 5,741,977 | A | 4/1998 | Agar et al. |
| 6,532,826 | B1 * | 3/2003 | Dou .................. G01F 1/712 73/861.04 |
| 7,654,151 | B2 | 2/2010 | Agar et al. |
| 7,661,302 | B2 | 2/2010 | Gysling |
| 7,717,000 | B2 | 5/2010 | Xie et al. |
| 7,908,930 | B2 | 3/2011 | Xie et al. |
| 7,942,065 | B2 | 5/2011 | Xie et al. |
| 8,536,883 | B2 | 9/2013 | Xie et al. |
| 8,606,531 | B2 | 12/2013 | Pinguet et al. |
| 8,641,813 | B2 | 2/2014 | Gysling |
| 8,915,145 | B1 | 12/2014 | Van Orsdol |
| 2005/0241410 | A1 | 11/2005 | Wium |
| 2009/0000389 | A1 | 1/2009 | Redon |
| 2010/0145634 | A1 * | 6/2010 | Pinguet .................. G01F 1/46 702/45 |
| 2010/0198531 | A1 | 8/2010 | Bell et al. |
| 2010/0305880 | A1 | 12/2010 | Oddie |
| 2011/0283809 | A1 | 11/2011 | Pihlaja et al. |
| 2012/0000643 | A1 | 1/2012 | Bruun et al. |
| 2012/0017697 | A1 | 1/2012 | Benzo et al. |
| 2012/0242081 | A1 | 9/2012 | Keays et al. |
| 2012/0325751 | A1 | 12/2012 | Renick et al. |
| 2013/0206420 | A1 | 8/2013 | McHugh et al. |
| 2013/0327154 | A1 | 12/2013 | Xie et al. |
| 2014/0007696 | A1 | 1/2014 | Al-Hadhrami et al. |
| 2014/0041463 | A1 | 2/2014 | Vethe et al. |
| 2014/0137643 | A1 | 5/2014 | Henry et al. |
| 2014/0331783 | A1 | 11/2014 | Xie |
| 2015/0185062 | A1 | 7/2015 | Ahmad et al. |
| 2017/0010139 | A1 | 1/2017 | Vilstrup et al. |
| 2018/0143052 | A1 | 5/2018 | Xie et al. |

FOREIGN PATENT DOCUMENTS

| | | |
|---|---|---|
| EP | 1744131 A1 | 1/2007 |
| EP | 2171407 A1 | 4/2010 |
| WO | WO2002088519 A1 | 11/2002 |

OTHER PUBLICATIONS

International Preliminary Report on Patentabilitly issued in the related PCT application PCT/US2016/041036 dated Jan. 9, 2018 (10 pages).
International Search Report and Written Opinion issued in the related PCT application PCT/US2016/041036 dated Nov. 1, 2016 (14 pages).
International Search Report and Written Opinion issued in the related PCT application PCT/US2018/023447 dated Jul. 9, 2018 (15 pages).
Office action issued in the related U.S. Appl. No. 15/973,133 dated Jul. 30, 2018 (16 pages).
Office Action issued in the related RU application 2017141565 dated Jun. 20, 2018 (12 pages).
Office Action issued in the related RU Application 2018104459 dated Sep. 20, 2018 (14 pages).
European Search Report issued in the related EP Application 168218901 dated Nov. 7, 2018 (3 pages).
Office Action issued in the related EP Application 16821890.7 dated Nov. 19, 2018 (3 pages).
Office Action issued in the related CN application 201680039205.8, dated Nov. 23, 2018 (13 pages).
Decision of Grant issued in the related RU application 2017141565 dated Nov. 30, 2018 (18 pages).
Office Action issued in the related U.S. Appl. No. 15/570,497 dated Apr. 18, 2019, 35 pages.

* cited by examiner

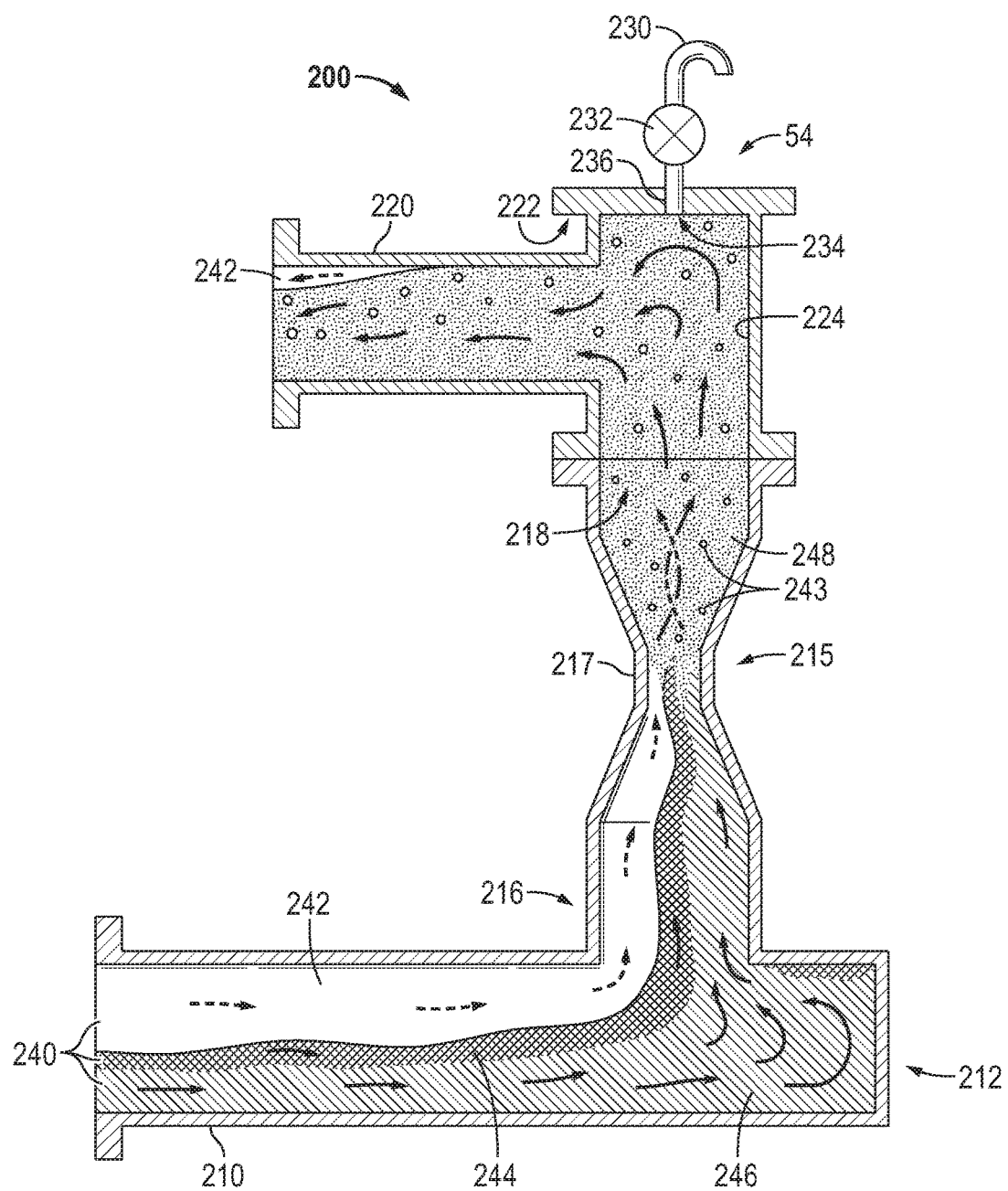

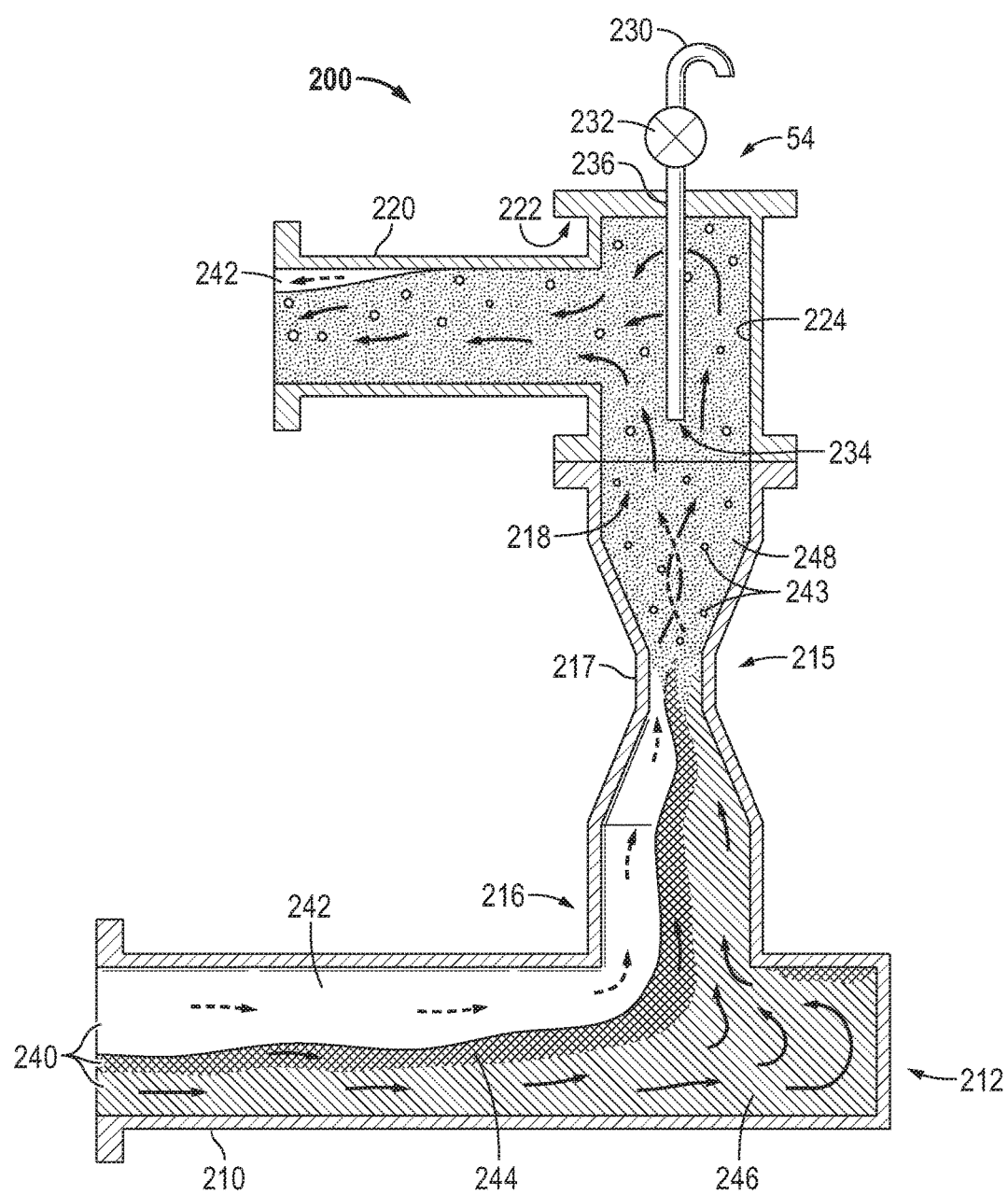

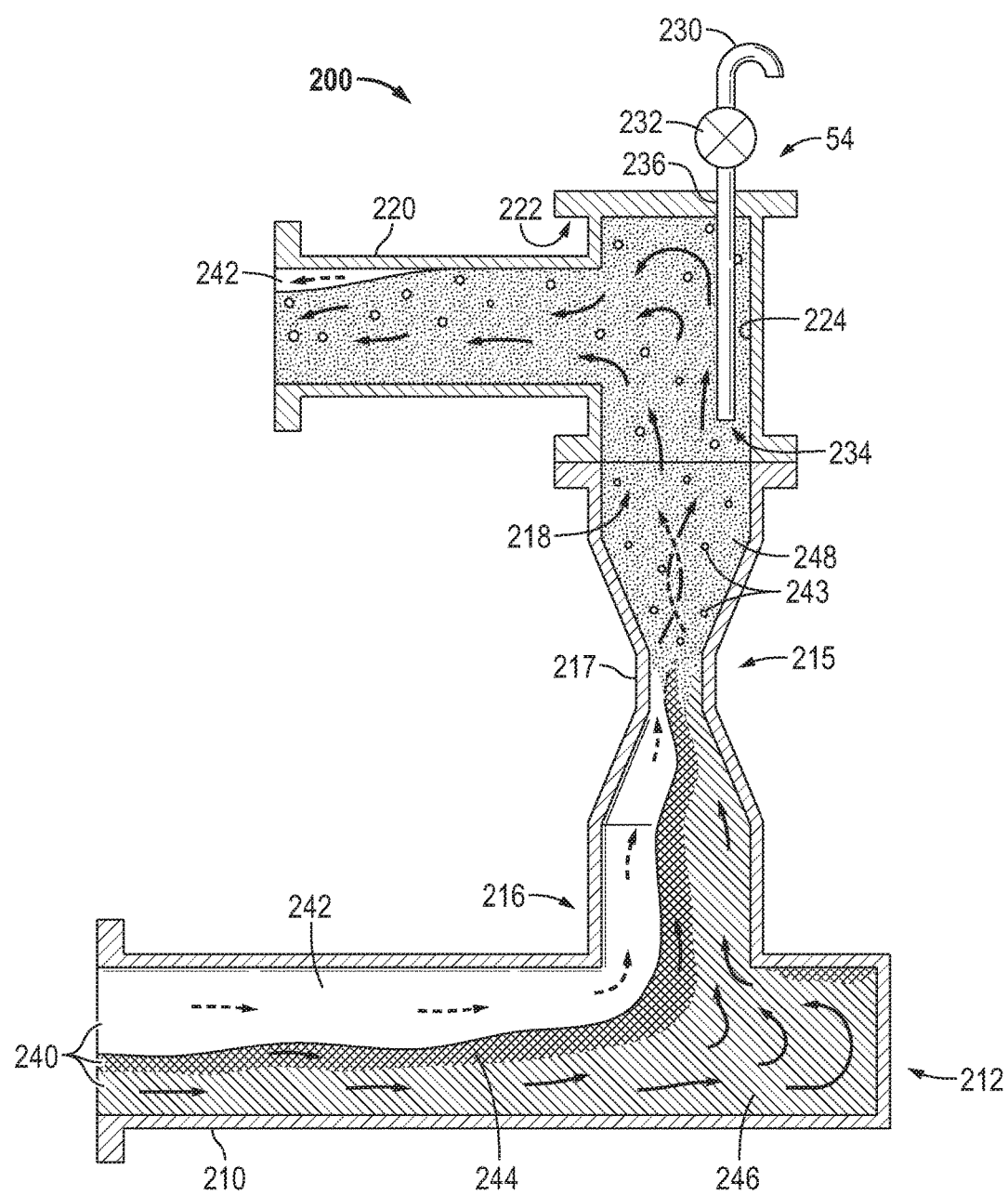

REPRESENTATIVE SAMPLING OF MULTIPHASE FLUIDS

CROSS-REFERENCE TO RELATED APPLICATIONS

The present application is related to U.S. patent application Ser. No. 14/793,404, which was filed on Jul. 7, 2015, and is incorporated herein by reference in its entirety.

BACKGROUND

Field

The present disclosure relates to techniques for measuring multiphase flows from wellbores. More particularly, the present disclosure relates to tools and methods for obtaining samples of multiphase fluid from a mobile multiphase flowmeter system.

Description of the Related Art

In many hydrocarbon well applications, various test procedures are employed to evaluate characteristics of the produced well fluid or other reservoir characteristics. Often, the produced well fluid contains a mixture of phases, such as a mixture of oil, water, gas, and solids or other components. Test procedures have been employed to evaluate the phases of produced fluids from specific wells. For example, various types of well testing equipment utilize multiphase flow meters to measure the various phases of the produced fluid. Samples of the multiphase fluid flowing in multiphase flow meters may be acquired as needed to use for various purposes, such as cross-checking the measurement quality of or calibrating the multiphase flow meter, obtaining liquid and gas samples at line pressure and temperature for pressure-volume-temperature (PVT) analysis, determining water chemistry (salt species, salinity changes, hydrate inhibitor content), providing flow assurance (effectiveness of hydrate/scale/corrosion inhibitor injections), analyzing oil and gas composition, and managing reservoir production, modeling, and compartmentalization, to list a few. Samples may also be used to determine water-liquid-ratios (WLR) or base sediment and water (BSW) of the multiphase fluid flowing from the well at different times. Representative sampling of multiphase fluid is thus very desirable.

SUMMARY

In general, disclosed herein are methods, systems, and apparatuses for sampling a multiphase fluid. In some embodiments, the method includes flowing a multiphase fluid comprising an oil phase and a water phase through a first conduit, the oil phase and water phase at least partially separating in the first conduit, mixing together the oil phase and water phase to form a mixed bulk liquid phase by flowing the multiphase fluid through a flow mixer toward a second conduit downstream the flow mixer, sampling a portion of the mixed bulk liquid phase at location at or within the second conduit, wherein the sampled portion of the mixed bulk liquid phase has a water-to-liquid ratio (WLR) representative of the pre-mixed oil phase and water phase.

In some embodiments, an apparatus for sampling a multiphase fluid includes a first conduit comprising a first blind leg, a flow mixer coupled to the first conduit proximate the blind leg, a second conduit comprising a second blind leg coupled to the flow mixer proximate the second blind leg, the flow mixer disposed in between the first and second conduit, and a sampling line coupled to a sampling port in the second blind leg, the sampling line disposed along the exterior of the second blind leg.

However, many modifications are possible without materially departing from the teachings of this disclosure. Accordingly, such modifications are intended to be included within the scope of this disclosure as defined in the claims.

BRIEF DESCRIPTION OF THE DRAWINGS

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

FIG. 2 is an illustration showing a cross-sectional view of a sampling apparatus, according to some embodiments of the disclosure.

FIGS. 3A and 3B are illustrations of cross-sectional views of alternative sampling apparatuses, according to some embodiments of the disclosure.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

With respect to certain embodiments of the present disclosure, a methodology and system are provided to facilitate efficient testing and sampling of flows of well effluent or well treatment fluid to determine, for example, the constituents, e.g. phases, of the fluid. In, for example, well testing applications, the methodology and system provide a mobile, modular system which is easily and quickly adapted to the parameters, e.g. flow rates, of a given well and provide easy obtainable multiphase fluid samples. According to some embodiments, a modular flow meter system comprises a plurality of modules which each have a multiphase flow meter coupled into a flow circuit. Portions of the flow circuits may be selectively opened and closed to enable controlled routing of the fluid being tested through the desired multiphase flow meter or meters. According to some embodiments, the modular flow meter system may comprise a skid, e.g. a modular skid, onto which the mobile multiphase flow meter production test platforms are mounted.

Figure 1:
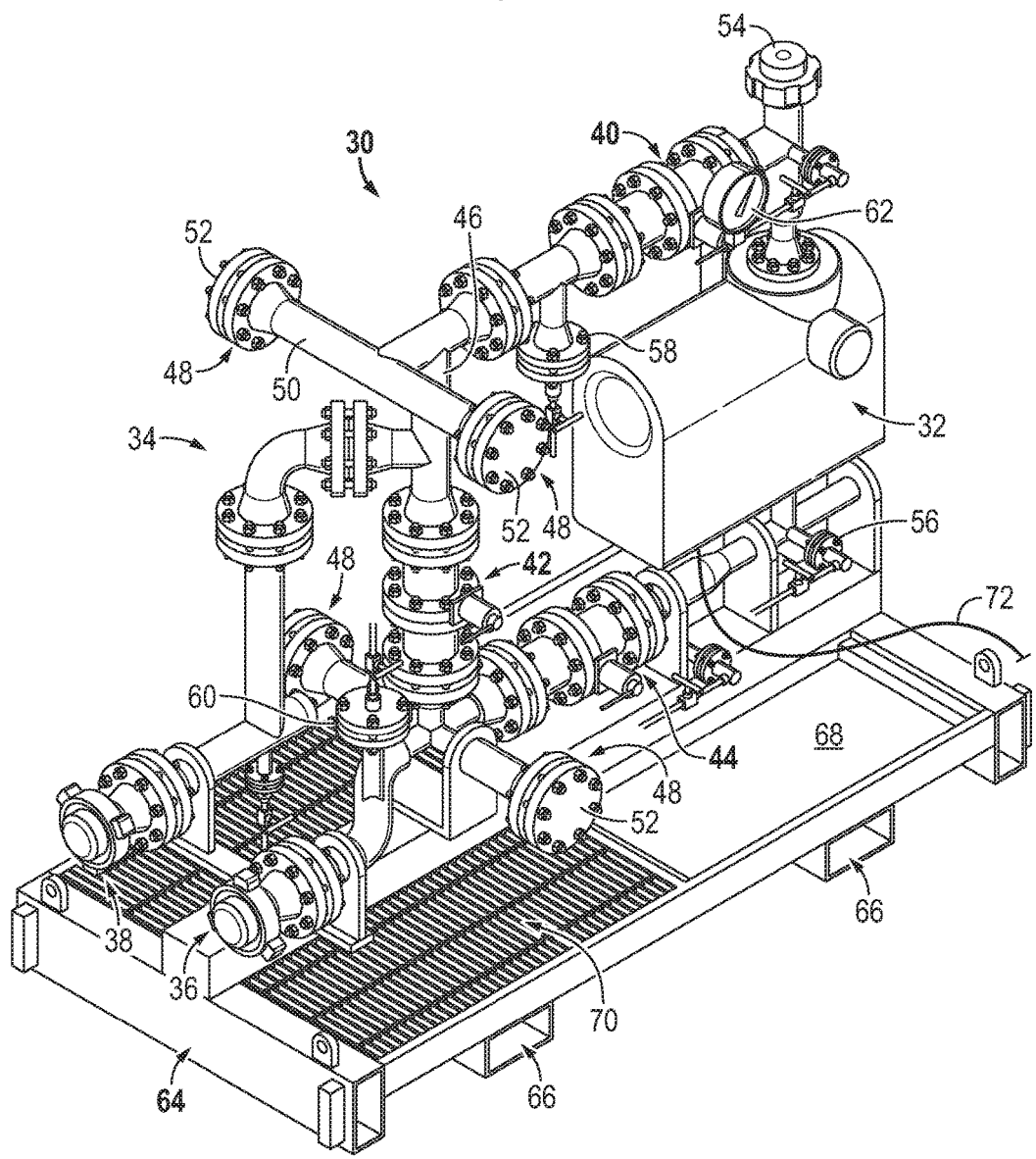
FIG. 1 is an illustration of an example of a flow test module which may be coupled into a modular flow meter system for evaluating flows of fluids, according to some embodiments of the disclosure.

Referring generally to FIG. 1, an example of a flow test module 30 is illustrated as comprising a flow meter 32, e.g. a multiphase flow meter, coupled into a flow circuit 34. By way of example, the flow meter 32 may comprise a Vx Spectra™ multiphase flow meter available from Schlumberger Technology Corporation for use in analyzing the flow rates and ratios of fluid constituents, such as oil, water, and gas in a produced well fluid. However, a variety of other types of flow meters 32 may be used in combination with flow circuit 34 depending on the parameters of a given fluid testing application. The flow circuit 34 comprises an inlet 36 through which the fluid to be tested, e.g. production well fluid, flows into the flow circuit 34. The flow circuit 34 also comprises an outlet 38 through which the fluid flow is discharged from the flow circuit 34. If the flow circuit 34 is configured to enable testing, the fluid is directed through flow meter 32 and is ultimately discharged through the outlet 38 of flow circuit 34.

However, module 30 is constructed so that flow through flow circuit 34 and flow meter 32 is easily controllable. In the embodiment illustrated, the flow of fluid along flow circuit 34 may be controlled via a plurality of isolation valves 40, 42 and 44. The valves 40, 42, 44 may be individually actuated between positions open to flow and closed to flow. For example, the flow of fluid entering inlet 36 may be directed through flow meter 32 by opening valves 40 and 44 while closing valve 42 located along a flow circuit bypass 46, e.g. a bypass manifold. However, the flow meter 32 is easily bypassed, for example, by closing valves 40, 44 while opening valve 42 in bypass 46. As described in greater detail below, the valves 40, 42, 44 may be used in combination with valves of corresponding modules 30 to direct desired flows of fluid through a specific flow meter 32. In the embodiment illustrated, valves 40, 42, 44 may be in the form of ball valves although other types of valves, e.g. sleeve valves, plug valves, other types of rotary valves, may be suitable for a variety of applications.

To facilitate coupling of module 30 with additional flow test modules 30, the flow circuit 34 comprises a plurality of flow connector ends 48. The flow connector ends 48 are disposed on flow conduits 50 of flow circuit 34 and are oriented for coupling with corresponding flow connector ends 48 of corresponding modules 30. When not in use, the flow connector ends 48 may be "blanked off" by securing blanks 52 to the flow connector ends 48 so as to prevent fluid flow therethrough. By way of example, the flow connector ends 48 may comprise flanges to which the blanks 52 are secured by suitable fasteners, e.g. threaded fasteners.

Depending on the application, flow circuit 34 may comprise a variety of other components or features. For example, the flow circuit 34 may comprise an access port 54 above flow meter 32 and a base sediment and water (BSW) port 56 below the flow meter 32. The flow circuit 34 also may comprise, for example, a liquid sampling port 58 and a gas sampling port 60. Various sensors, such as a pressure gauge 62, also may be positioned along flow circuit 34.

In some embodiments, the flow circuit 34 and flow meter 32 may be mounted on a portable skid 64. Skid 64 also may be modular for use with corresponding skids 64 of corresponding flow test modules 30. In some applications, the skids 64 of corresponding modules 30 may be coupled together to form an overall skid which facilitates movement of the module/modules 30 between locations, e.g. between well sites, to enable fluid testing procedures. The skids 64 are constructed to enhance the mobility and transportability of the modules 30 and may include features, such as forklift pockets 66 which facilitate lifting and movement of the skids 64 via forklift. In some applications, forklifts may be used to load and unload the modules 30 with respect to a suitable transport vehicle. Each skid 64 may comprise a variety of other features to facilitate aspects of given application. Examples of such features include drip pans 68 and grates 70.

Signals, e.g. informational data and/or control signals, may be communicated from and/or to flow meter 32 via a communication line or lines 72. For example, data on the phase composition of fluids flowing through multiphase flow meter 32 may be output through communication lines 72. Additionally, at least one of the communication lines 72 may be used to carry control signals to controllable isolation valves 40, 42, 44. In this manner, specific isolation valves 40, 42, 44 may be actuated to the desired open or closed position via an appropriate command/control signal. Depending on the type of isolation valve, the corresponding communication line 72 may be an electrical line, hydraulic line, or other suitable control line(s).

As previously discussed the flow circuit 34 may include an access port 54 above flow meter 32 and a BSW port 56 below the flow meter 32. Alternatively, access port 54 can be modified to obtain a liquid sample for BSW or WLR measurement that is better and more accurate or representative than a liquid sample obtained using BSW port 54. To that end, some embodiments, devices, apparatuses, and methods for sampling a multiphase fluid are disclosed herein that may utilize port 54 instead of port 56 for sampling multiphase fluids.

FIG. 2 illustrates an apparatus 200 for sampling a multiphase fluid or a portion thereof, such as a liquid phase of a multiphase fluid, where the liquid phase includes two different liquids. Apparatus 200 may include portions of the flow test module 30 including portions of the flow circuit 34. A first conduit 210 comprises a first blind leg 212. The BSW port 56 may be located proximate the first blind leg 212 as shown in FIG. 1. A flow mixer 215 is coupled to the first conduit 210 proximate the first blind leg 212. The flow mixer 215 includes an inlet 216 and an outlet 218.

A second conduit 220 comprising a second blind leg 222 is coupled to the flow mixer 215 proximate the second blind leg 222, such that the outlet 218 of the flow mixer 215 faces the second blind leg 222. The flow mixer 215 is disposed in between the first and second conduits 210, 220. The flow mixer 215 may comprise a venturi 217. The flow mixer 215 may also comprise a multiphase venturi flow meter 32, as shown in FIG. 1. The first conduit 210 may be disposed in a substantially horizontal position as shown in FIG. 2. The flow mixer 215, however, is disposed in at least one of a substantially vertical position and a position substantially perpendicular to the first conduit 210, as generally shown in FIGS. 1 and 2. Substantially horizontal means that the first conduit 210 may vary as much as ±10° from horizontal, e.g. between −10° and +10° in relation to the horizontal baseline of the mounting surface of portable skid 64. Substantially vertical means the flow mixer 215 may vary as much as ±10° from vertical, e.g. between 80° and 100° in relation to the horizontal baseline of the mounting surface of portable skid 64. Substantially perpendicular means the flow mixer 215 may vary as much as ±10° from perpendicular (90°) to the first conduit 210, e.g. between 80° and 100° in relation to the first conduit 210.

A sampling line 230 is coupled to a sampling port 236, such as located in access port 54, in the second blind leg 222. The sampling line 230 is disposed along the exterior of the second blind leg 222, and may include a valve 232 (which may be a double-block valve) for opening and closing the sampling line 230 to obtain a sample of multiphase fluid.

FIGS. 3A and 3B show alternative placements of the sampling line 230 with respect to the second conduit 220. FIG. 3A shows the sampling line 230 extending through the sampling port 236 and into the second conduit 220. An opening 234 of the sampling line 230 faces an outlet 218 of the flow mixer 215. The sampling line 230 may be placed in a centered location with respect to the outlet 218 and the multiphase flow. In FIG. 3B, the sampling line 230 extends through the sampling port 236 and into the second conduit 220. In this embodiment, the opening 234 of the sampling line 230 faces an outlet 218 of the flow mixer 220 and is positioned adjacent an inner wall 224 of the second conduit 220.

Regardless of the exact location of the sampling line 230, the opening 234 of sampling line 230 is oriented and positioned such that a sample of mixed bulk liquid phase 248 is taken at a single-point either within the multiphase fluid 240 within the second conduit 220 proximate the second blind leg section 222, as shown in FIGS. 3A and 3B or at the second blind leg section 222 as shown in FIG. 2, i.e. the sample port 54.

The first and second conduits 210, 220, the blind leg sections 212, 222, the flow mixer 215 in-between first and second conduits 210, 220, and the sampling line 230 coupled with the sampling port 236, which may be located in the blind leg section 222, together provide the WLR-representative liquid (oil and water) sampling apparatus 200. As will be described in more detail below, this arrangement provides a non-isokinetic sampling apparatus that is easier to operate and maintain than an isokinetic sampling apparatus and method, which are generally necessary to obtain flow-rate representative gas and liquid samples. Isokinetic sampling means that the linear velocities of the phases of a multiphase fluid entering the sampling port/probe opening are maintained the same as the linear velocities of the multiphase fluid before the sample is taken. Isokinetic sampling may be achieved by nulling the differences in the pressure measured at the pipe wall of the main-stream conduit (at a location upstream of the sampling port/probe opening) and that measured at the pipe wall of the sample-stream conduit (near the sampling port/probe opening), by controlling sample-extraction flow rate.

Isokinetic sampling is known to provide gas and liquid samples that are representative of the gas-liquid-ratio (GLR) of that of the multiphase fluid from the wellhead, and to provide oil and water liquid samples of multiphase fluid that are representative of the WLR of that of the multiphase fluid from the wellhead. The sampling apparatus 200 shown in FIG. 2 provides WLR-representative liquid (oil and water) samples, without the need of controlling sample-extract flow rate as required in an isokinetic sampling apparatus. Referring back to FIGS. 2-3B, the method of sampling a multiphase fluid 240 includes flowing a multiphase fluid 240 through the first conduit 210. The multiphase fluid 240 may comprise a liquid phase comprising two or more liquid phases or components, such as an oil phase 244 and a water phase 246. The multiphase fluid may also include a gaseous phase 242. The flow of the gaseous phase 242 and the liquid phase, including oil phase 244 and water phase 246, through the corresponding section of the flow circuit 34 (shown in FIG. 1, near the BSW sampling port 56 that is located at the horizontal blind-leg upstream of the flowmeter 32 and the vertical blind-leg is located at the access port 54), including conduits 210, 220 and flow mixer 215, are indicated by the dashed and solid arrows respectively. The first conduit has a first blind leg section 212. As shown in the FIGS. the oil phase 244 and water phase 246 tend to at least partially separate in the first conduit 210. The oil phase and water phase are then mixed together to form a mixed bulk liquid phase 248. The mixing of the two liquid phases performed by flowing the multiphase fluid 240 through a flow mixer 215 toward a second blind leg section 222 of a second conduit 220 downstream the flow mixer 215.

The flow mixer 215 in some embodiments may be a venturi device 217. The flow mixer 215 may also be a multiphase venturi flow meter 32. The flow mixer 215 not only produces a well-mixed oil-water liquid phase (the mixed bulk liquid phase 248), but in embodiments where the multiphase fluid 240 includes a gaseous phase 242, the gaseous phase 242 tends to be better mixed with the mixed bulk liquid phase 248 after passing through the flow mixer 215, as illustrated by the bubbles 243 shown after passing through the venturi 217 in FIG. 2. As the multiphase fluid 240 flows through the flow circuit 34 to the second conduit 220, some of the gas bubbles 243 escape the mixed bulk liquid phase 248, possibly forming a separated gaseous phase 242 shown as the multiphase fluid exits the second conduit 220.

A venturi 217 acts as a good oil-water mixer due to increased flow velocity therein and hence increased turbulent mixing. At the venturi throat section, a high gas-liquid velocity region is present which may provide a good oil-water mixer. High velocity gas enhances the liquid mixing and the upward momentum. A sampling port 234 located downstream of the flow mixer after the venturi outlet section 218 provides sample extraction in the same direction as the incoming flow, thereby providing low frictional loss for the sampled fluid flow entering the sampling line 230. A sample of the liquid phase taken from the sampling line 230 at this location provides a liquid phase sample that is better representative of WLR for the multiphase fluid itself (the pre-mixed oil phase and gas phase) than at the horizontal blind-leg location. In other words, the WLR of a liquid phase sample is representative of the ratio of the water-phase volumetric flow rate to the total liquid volumetric flow rate.

In some isokinetic samplers that are used for high gas-volume-fraction (GVF) multiphase fluids, at least one orifice plate may be used as a flow conditioner to shed and break-up slow-moving liquid film on a pipe inner-wall into the fast-moving gas-core stream, and thereby homogenize the liquid droplets into the gas stream. It is believed that a venturi cannot shed/breakup wet-gas liquid film as effectively as an orifice-plate. But, it is believed that a vertically installed venturi may increase the multiphase fluid flow gas-liquid velocity/momentum, where GVF range is from 0 to 99%, by multiple-fold at the venturi throat section in order to enhance oil/water mixing and gas/liquid mixing. It is believed that as much as a four-fold velocity increase may be achievable for a beta 0.5 venturi (beta is the ratio of Venturi throat-diameter to its inlet-diameter) and a sixteen fold increase for the liquid flow momentum ($\rho v^2$). The enhanced gas-liquid flow velocity/momentum will mix low-density contrast, vertically-flowing (gas-entrained) oil-water liquid mixture very well. It is believed that because of the low-density contrast between venturi-aided well-mixed oil and water phases, the sampled liquid will have a WLR representative of the multiphase fluid without the need of practicing dP-dulling isokinetic sampling means (as described before). That is, the sample-extraction flow velocity can be unequal to the incoming multiphase fluid flow velocity.

In some embodiments, the first conduit 210 is disposed in a substantially horizontal position compared to the skid surface 68. The flow mixer 215 may also be disposed in at least one of a substantially vertical position and a position substantially perpendicular to the first conduit 210. In some embodiments, the method includes flowing the multiphase fluid 240 through a flow mixer 215 toward the second blind leg section 222 in at least an upward direction and/or against gravitational pull.

A portion of the mixed bulk liquid phase 248 is sampled at location proximate the second blind leg section, such as at sampling port 236 and opening 234 of sampling line 230. The sampled portion of the mixed bulk liquid phase 248 has a water-to-liquid ratio (WLR) representative of the pre-mixed oil phase 244 and water phase 246. By using the described method and devices, liquid sampling representative of the WLR of the pre-mixed liquid phase of the multi-phase fluid is achievable in non-isokinetic conditions. Moreover, the ability to acquire a liquid phase sample having a WLR representative of liquid phase of the multiphase fluid is possible over a wide range of gas volume fractions (GVF) such as less than 99% GVF.

In some embodiments, the method also includes determining the water-to-liquid ratio (WLR) of the sample portion of the mixed liquid phase 248. Various methods may be used to determine the WLR of the sampled mixed liquid phase 248, an oil-water mixture. For example, for easily separated oil-water mixtures, the sampled oil-water mixture can be determined by sampling the oil-water mixture using a measuring cylinder, known of those skilled in the art, and reading off the measured water and liquid volumes or levels. In cases where the oil-water mixture does not easily separate, a sealed measuring cylinder can be centrifuged to better separate the oil-water mixture, and then read off the measured water and liquid volumes or levels.

In some embodiments, sampling the portion of the mixed bulk liquid phase 248 is taken at a single-point either within the second conduit 220 proximate the second blind leg section 222 or at the second blind leg section 222. For example, as shown in FIG. 2, the single-point is the opening 234 of the sampling line 230 located at an inner wall of the blind leg section 222. Alternatively, single-point sampling is located within the multiphase fluid within the second conduit 220 proximate the second blind leg section 222. For example, as shown in FIGS. 3A and 3B, the single-point sampling is the opening 234 of the sampling line 230 that extends into the multiphase fluid within the second conduit 220 at a location adjacent an outlet 218 of the flow mixer 215, where the gas-liquid velocity and concentration are higher. Sampling the portion of the mixed liquid phase may also be taken at a location adjacent an inner wall 224 of the second conduit 220 and downstream the flow mixer 215. The arrangement shown in FIG. 3B may be desired in higher GVF wells where liquid may be richer near the pipe-wall region. The flow path direction of the sampling port 236 and opening 234 of the sampling line 230 is aligned with the incoming (vertical upward) flow direction of the multiphase fluid 240, which provides low frictional loss of sampled flow. These features may reduce oil/water re-separation and the sampling time to obtain sufficient volume of the sampled liquid, especially at high GVFs.

As described previously, the BSW sampling port 56 for a modular multiphase flowmeter is shown to be located at the horizontal blind leg section 212 (for example of the multiphase flow meter 32). It has been found that in the horizontal blind leg section 212 (FIG. 2), there may be a tendency of poor oil phase and water phase mixing due to relatively low liquid velocity and oil-water stratification due to gravitational force. Moreover, the BSW port 56 for sampling in the horizontal blind-leg 212 does not face the incoming flow direction, but is on the side (see FIG. 1). For those reasons, the horizontal blind-leg 212 has been found to be a desirable location where a liquid-rich (but not necessarily WLR-representative) sample may be taken. The horizontal blind-leg 212 has also been found to be a preferred location where water is rich at its underside to facilitate water salinity detection, even at low WLRs, by the use of a microwave conductivity probe. Liquid samples captured at this location, however, tend to have a higher WLR than the reference, except at GVF>~95%, where high-gas flow enhances the oil and water mixing in the end of the blind-leg. In other words, at GVF<~95%, the liquid phase sampled from the horizontal blind leg section 212 is largely not representative of the WLR of multiphase fluid 240 as it flows from a wellhead and to the flow test module 30.

Figure 4:
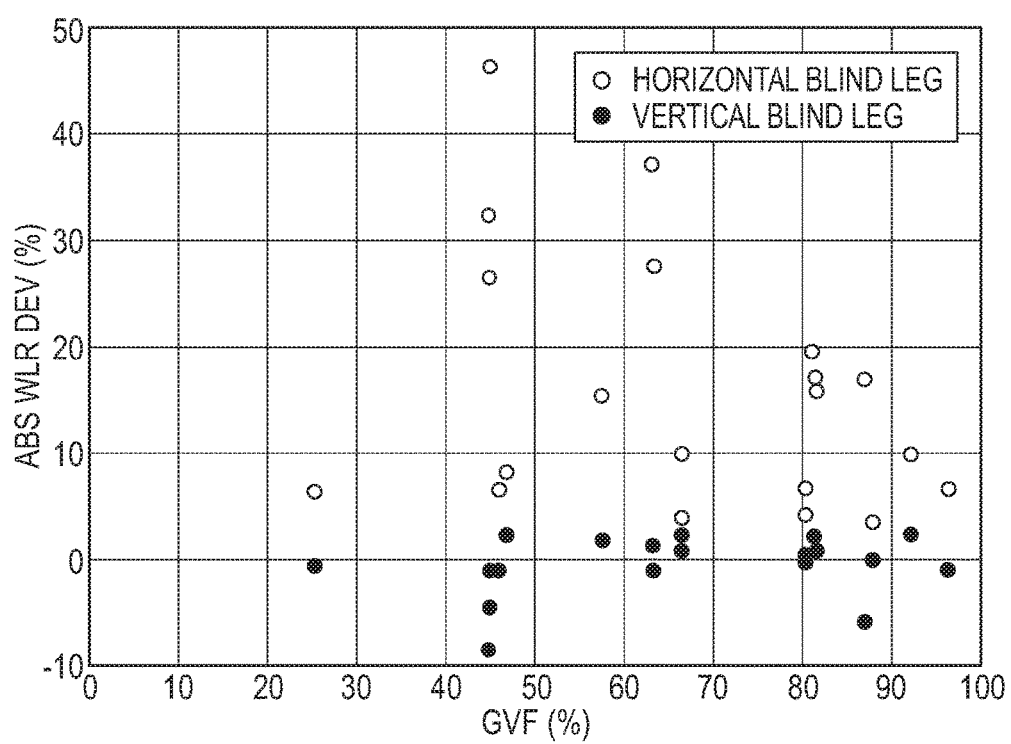
FIG. 4 illustrates a graph of the absolute error of WLR of sampled multiphase fluid at different locations of the flow test module.

As shown in FIG. 4, extensive experimental flow-loop tests have shown that the liquid WLR measurement from the multiphase flow samples gathered from the BSW sampling port 56 in the horizontal blind-leg inlet of the flow meter 32 tend to have larger error (with respect to the flow-loop reference WLR) than that gathered from the sampling line opening 234 placed at the access port 54. FIG. 4 shows flow-loop test results of a multiphase venturi flowmeter where the WLR absolute error (with respect to a flow loop reference WLR) of multiphase flow samples gathered from a BSW port 56 (at the horizontal blind leg 212) and compared to samples gathered from the sample port line opening 234 at the vertical blind-leg section 222. As shown in the graph, the samples gathered from the vertical blind-leg section 222 are more consistent and less affected by the upstream piping and flow conditions.

In some applications, the horizontal blind leg section in the first conduit may be replaced by a horizontal section with a first 90-degree pipe elbow connection interconnecting the horizontal conduit with a second vertical conduit, with a flow mixer such as a Venturi disposed in between. The vertical blind-leg section in the second conduit may also be replaced by a second 90-degree pipe elbow connection interconnecting outlet of the flow mixer with the horizontal exit pipe of the second conduit. A sampling probe may be inserted vertical downwards from the second 90-degree elbow with the sampling probe opening located near the outlet of the flow mixer.

In subsea applications, a multiphase flow may flow through a horizontal blind-leg inlet and then flow vertically downwards through a multiphase flow meter comprising a Venturi. The Venturi may be used as a flow mixer for the vertically downward multiphase fluid. Sampling of mixed bulk liquid may be performed downstream of the flow mixer, with the sampling probe opening aligned facing the downwardly incoming mixed bulk liquid flow.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

The invention claimed is:

1. A method of sampling a multiphase fluid, comprising:
   flowing a multiphase fluid comprising an oil phase and a water phase through a first conduit, the oil phase and water phase at least partially separating in the first conduit;
   mixing together the oil phase and water phase to form a mixed bulk liquid phase by flowing the multiphase fluid through a flow mixer toward a second conduit downstream of the flow mixer;
   sampling a portion of the mixed bulk liquid phase at a location at or within the second conduit, wherein the sampled portion of the mixed bulk liquid phase has a water-to-liquid ratio (WLR) representative of the premixed oil phase and water phase;
   wherein the first conduit has a first blind leg section and the second conduit has a second blind leg section, and wherein an outlet of the flow mixer faces the second blind leg section of the second conduit and the sampled portion of mixed bulk liquid phase is taken at a location proximate the second blind leg section.

2. The method of claim 1, wherein sampling the portion of the mixed bulk liquid phase is a non-isokinetic sampling.

3. The method of claim 1, wherein the flow mixer is a venturi.

4. The method of claim 1, wherein the flow mixer is a multiphase venturi flow meter.

5. The method of claim 1, further comprising:
   determining the water-to-liquid ratio (WLR) of the sampled portion of the mixed liquid phase.

6. The method of claim 1, wherein sampling the portion of the mixed liquid phase is taken at a single-point either within the multiphase fluid within the second conduit proximate the second blind leg section or at the second blind leg section.

7. The method of claim 1, wherein sampling the portion of the mixed liquid phase is taken within the second conduit at a location adjacent an outlet of the flow mixer.

8. The method of claim 1, wherein sampling the portion of the mixed liquid phase is taken at a location adjacent an inner wall of the second conduit and downstream of the flow mixer.

9. The method of claim 1, wherein the first conduit is disposed in a substantially horizontal position.

10. The method of claim 1, wherein the flow mixer is disposed in at least one of a substantially vertical position and a position substantially perpendicular to the first conduit.

11. The method of claim 1, wherein flowing the multiphase fluid through a flow mixer toward the second blind leg section comprises flowing the multiphase fluid in at least one of an upward direction and against gravitational pull.

* * * * *